United States Patent [19]

Simon et al.

[11] Patent Number: 5,661,405

[45] Date of Patent: Aug. 26, 1997

[54] ELONGATE SENSOR HAVING POLYMERIC ELECTRODES FILLED WITH CONDUCTIVE PARTICLES AND HAVING BRAIDED SLEEVES

[76] Inventors: Jay S. Simon, 211 State Ct.; Morris Simon, 2050 Mallard Dr., both of Northbrook, Ill. 60062

[21] Appl. No.: 554,433

[22] Filed: Nov. 6, 1995

[51] Int. Cl.$^6$ ............................................. G01R 31/08
[52] U.S. Cl. .................. 324/697; 324/690; 324/696; 338/38; 73/304 R; 340/620; 174/11 R
[58] Field of Search ...................... 73/304 R, 304 C; 340/620; 338/38, 44; 174/11 R; 324/697, 696, 694, 690, 689

[56] References Cited

U.S. PATENT DOCUMENTS

| | | |
|---|---|---|
| 3,098,116 | 7/1963 | Jore et al. . |
| 3,437,924 | 4/1969 | Tocanne ........................... 324/690 |
| 3,732,556 | 5/1973 | Caprillo et al. . |
| 3,778,570 | 12/1973 | Shuman . |
| 3,824,460 | 7/1974 | Gustafson . |
| 4,136,823 | 1/1979 | Kullberg . |
| 4,319,232 | 3/1982 | Westphal et al. . |
| 4,418,712 | 12/1983 | Braley . |
| 4,843,305 | 6/1989 | Akiba . |
| 4,922,232 | 5/1990 | Bosich . |
| 5,008,650 | 4/1991 | Holberg . |
| 5,084,679 | 1/1992 | Löfgren . |
| 5,188,143 | 2/1993 | Krebs . |
| 5,190,069 | 3/1993 | Richards . |
| 5,315,291 | 5/1994 | Furr . |
| 5,341,128 | 8/1994 | Keyser et al. . |
| 5,410,255 | 4/1995 | Bailey . |
| 5,528,155 | 6/1996 | King ........................................ 324/690 |

Primary Examiner—Vinh P. Nguyen
Assistant Examiner—Jose M. Solis
Attorney, Agent, or Firm—Dressler, Rockey, Milnamow & Katz, Ltd.

[57] ABSTRACT

An elongate, flexible sensor for sensing an electrically conductive liquid, such as water, has two flexible electrodes extending along the sensor and two flexible sleeves extending therealong and being attached adhesively to each other along the sensor. Each electrode is a ribbon made from a carbon-filled, silicone rubber material. Each sleeve extends around an associated one of the electrodes and is braided from a filamentary, polyester material so as to define multiple apertures enabling such a liquid reaching the sensor to pass through the sleeves so as to cause a short circuit between the electrodes.

6 Claims, 2 Drawing Sheets

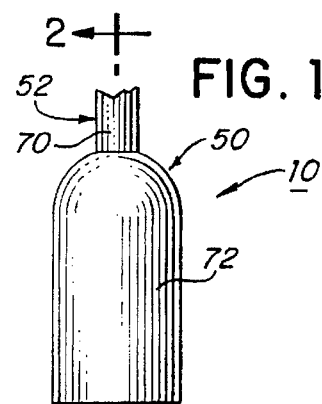
FIG. 1
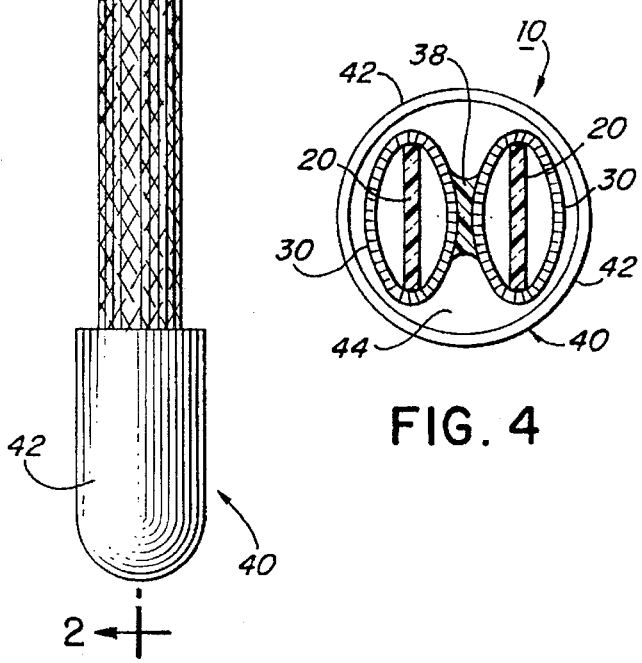
FIG. 3
FIG. 4
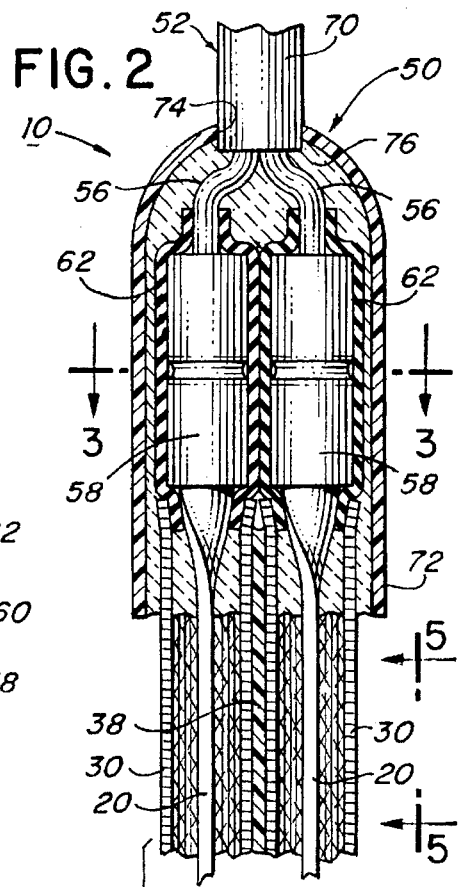
FIG. 2
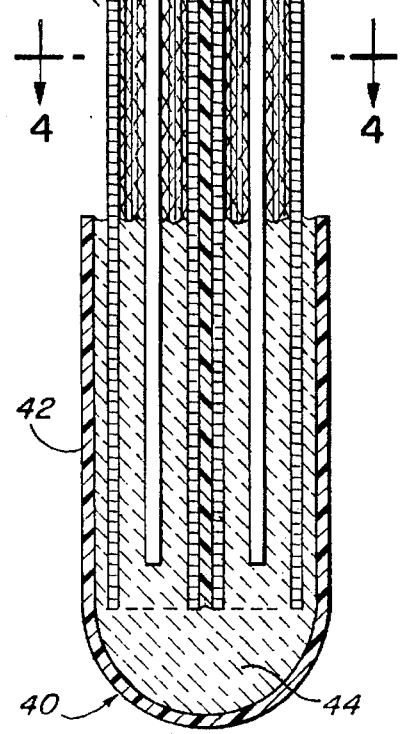

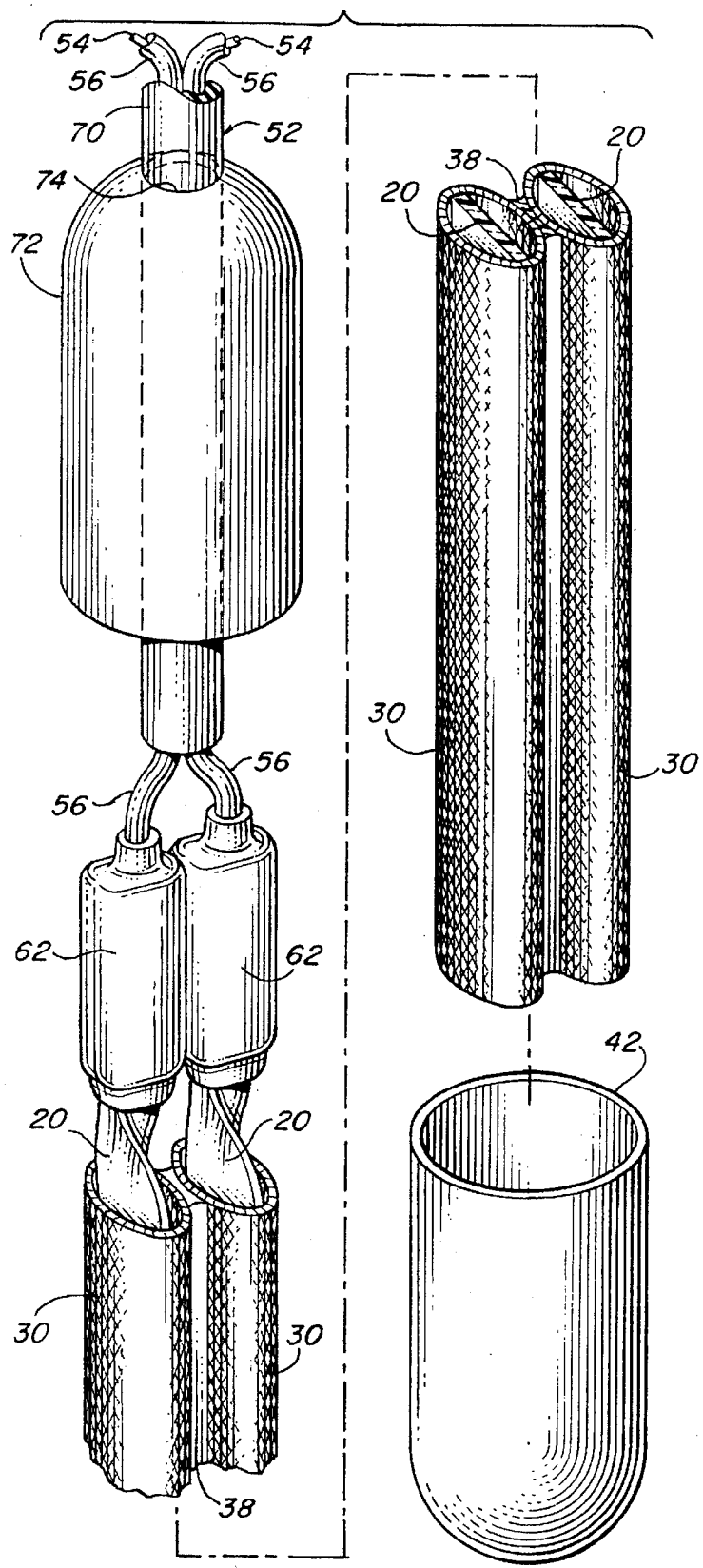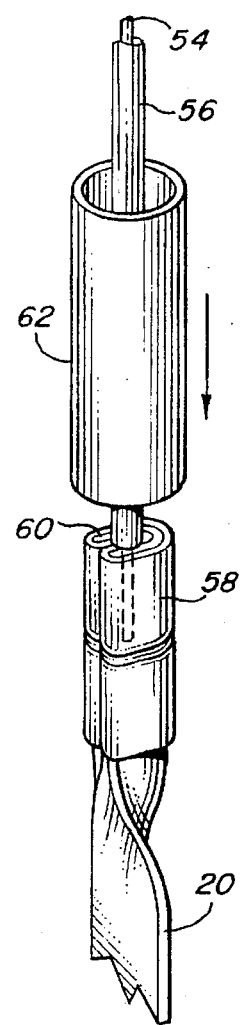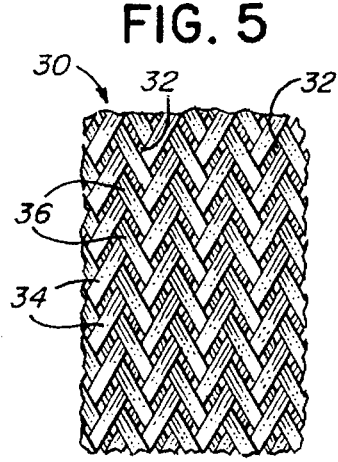

ELONGATE SENSOR HAVING POLYMERIC ELECTRODES FILLED WITH CONDUCTIVE PARTICLES AND HAVING BRAIDED SLEEVES

TECHNICAL FIELD OF THE INVENTION

This invention pertains to an elongate sensor for sensing an electrically conductive liquid, such as water. The sensor comprises two polymeric electrodes, each being filled with conductive particles, and two non-conductive sleeves, each extending around an associated one of the electrodes. The sleeves have multiple apertures enabling such a liquid reaching the sensor to pass through the apertures so as to cause a short circuit between the electrodes.

BACKGROUND OF THE INVENTION

Liquid sensors of a type employing metal electrodes are used widely in many industrial, commercial, and domestic applications. Typically, in such a sensor, metal electrodes are spaced from each other by some porous, notched, or slotted element permitting electrically conductive liquids, such as water, to cause a short circuit between such electrodes. Some known sensors of the type noted above employ short, rigid electrodes, and others employ elongate, flexible electrodes.

Liquid sensors of the type noted above are exemplified in numerous prior patents including Jore et al. U.S. Pat. No. 3,098,116, Caprillo et al. U.S. Pat. No. 3,732,556, Gustafson U.S. Pat. No. 3,824,460, Kullberg U.S. Pat. No. No. 4,136,823, Westphal et al. U.S. Pat. No. 4,319,232, Braley U.S. Pat. No. 4,418,712, Akiba U.S. Pat. No. 4,843,305, Bosich U.S. Pat. No. 4,922,232, Hofberg U.S. Pat. No. 5,008,650, Löfgren U.S. Pat. No. 5,084,679, Richards U.S. Pat. No. 5,109,069, and Bailey U.S. Pat. No. 5,410,255. Liquid sensors of related interest are exemplified in Shuman U.S. Pat. No. 3,778,570, Krebs U.S. Pat. No. 5,188,143 and Furr U.S. Pat. No. 5,315,291.

Generally, in a liquid sensor of the type noted above, such electrodes are made from single or multiple strands of copper. Although copper electrodes may be generally satisfactory for many applications, copper tends to corrode under common conditions, as when exposed to high humidity or other moisture or when subjected to galvanic corrosion due to a dissimilar metal. Because of its tendency to corrode, copper is unsuited for some applications. It is known for such copper electrodes to be gold-plated to inhibit their corrosion.

SUMMARY OF THE INVENTION

This invention provides an elongate, flexible sensor for sensing a liquid, such as water. The liquid sensor provided by this invention does not require such copper or other metal electrodes.

According to a first aspect of this invention, the sensor comprises two flexible electrodes extending along the sensor, each electrode being made from a rubber-like, polymeric material filled with conductive particles, and two flexible sleeves extending along the sensor and being attached to each other along the sensor, each sleeve extending around an associated one of the electrodes and being made from an electrically non-conductive material.

The sleeves have multiple apertures enabling such a liquid reaching the sensor to pass through the apertures so as to cause a short circuit between the electrodes. The sleeves may be advantageously braided from a filamentary material, preferably a monofilamentary, polyester material, so as to define such apertures. The sleeves may be er along the sensor.

Each electrode may be advantageously made from a carbon-filled, silicone rubber material. Preferably, each electrode is a ribbon made from the carbon-filled, silicone rubber material.

According to a second aspect of this invention, the sleeves described above may be advantageously employed with two flexible electrodes, even if the flexible electrodes are wire electrodes made from single or multiple strands of copper or another metal.

These and other objects, features, and advantages of this invention are evident from the following description of a preferred embodiment of this invention with reference to the accompanying drawings.

BRIEF DESCRIPTION OF THE DRAWINGS

FIG. 1 is a fragmentary, edge view of an elongate, flexible sensor constituting a preferred embodiment of this invention.

FIG. 2 is a fragmentary, longitudinal, sectional view of the elongate, flexible sensor shown in FIG. 1.

FIG. 3 is a sectional view taken along line 3—3 of FIG. 2, in a direction indicated by arrows.

FIG. 4 is a sectional view taken along line 4—4 of FIG. 2, in a direction indicated by arrows.

FIG. 5 is a planar development of a fragmentary view taken along line 5—5 of FIG. 2, in a direction indicated by arrows.

FIG. 6, on a larger scale, is a fragmentary, exploded view of the elongate, flexible sensor shown in FIGS. 1 through 5.

FIG. 7, on a similar scale, is a fragmentary, exploded detail showing assembly of certain elements shown in FIG. 6.

DETAILED DESCRIPTION OF THE PREFERRED EMBODIMENT

As shown in the drawings, an elongate, flexible sensor 10 for sensing a liquid, such as water, constitutes a preferred embodiment of this invention. Broadly, the sensor 10 comprises two flexible electrodes 20 extending along the sensor 10 and two flexible sleeves 30 extending along the sensor 10 and being attached to each other along the sensor 10. Each electrode 20 is a ribbon made from a rubber-like polymeric material filled with conductive particles, preferably a carbon-filled, silicone rubber material. Each sleeve 30 extends around an associated one of the electrodes. Each sleeve 30 is made from an electrically non-conductive material and has multiple apertures 32 enabling such a liquid reaching the sensor 10 to pass through the apertures 32 so as to cause a short circuit between the electrodes 20.

As shown, each sleeve 30 extends loosely around an associated one of the electrodes 20 and is braided from a filamentary, electrically non-conductive, polymeric material, so as to define the apertures 32. Thus, as shown in FIG. 5, each aperture 32 is defined by two warp filaments 34 and by two weft filaments 36. As shown, the sleeves 30 are attached to each other by an adhesive bead 38 extending along the sensor 10.

The preferred material for the electrodes 20 is the carbon-filled, silicone rubber material used for inner layers of LEAK-EDGE™ hydrocarbon sensors available commercially from One Plus Corp. of Northbrook, Ill. The silicone rubber material used for inner layers of such hydrocarbon sensors is carbon-filled so as to be electrically conductive and tends to absorb hydrocarbon liquids and to swell when exposed to such liquids. It should be here noted that such hydrocarbon sensors are available commercially with outer layers of unfilled, electrically insulative, silicone rubber material, which also tends to absorb hydrocarbon liquids and to swell when exposed to such liquids, but which is intended to prevent short-circuiting if such hydrocarbon sensors are exposed to water. However, the electrodes 20 do not have outer layers of untilled, silicone rubber material. It should be also noted that such hydrocarbon sensors are available commercially with outer sleeves, which extend loosely around such hydrocarbon sensors, and which are braided from a filamentary, electrically non-conductive, polymeric material, such as the preferred material for the sleeves 30.

The preferred material for the sleeves 30 is FLEX-GUARD™ expandable monofilament sleeving, which is a monofilamentary, polyester material, and which is available commercially from Alta Technologies, Inc. of Belie Mead, N.J. A preferred material for the adhesive bead 38 is SURE-BONDER™ all temperature glue, which is applied from glue sticks via high-temperature, low-temperature, and dial-temperature glue guns, and which is available commercially from FPC Corporation of Buffalo Grove, Ill. Other materials may be alternatively used for the sleeves 30 and for the adhesive bead 38.

At a distal end 40, the sensor 10 is provided with an electrically non-conductive cap 42, which is made from a resilient, polymeric material. The cap 42 is filled with a conventional potting material 44, in which end portions of the sleeves 30 and of the electrodes 20 are embedded. A preferred potting material is STYCAST 2651-40-FR filled epoxy resin, which is available commercially from Electro Insulation Corporation of Arlington Heights, Ill. At a proximal end 50, the sensor 10 is connected to an electrical cable 52. The electrical cable 52 comprises two wire conductors 54, each having an electrically insulative sleeve 56. Each electrode 20 is connected physically and electrically to an associated one of the wire conductors 54, via a copper connector 58, which is crimped around a polymeric spacer 60, and which is protected by a heat-shrunk, polymeric sleeve 62. The electrical cable 52 also comprises an electrically insulating sleeve 70 around the sleeves 52. At the proximal end 50, the sensor 10 is provided with an electrically non-conductive cap 72, which is similar to the cap 42, except that the cap 72 has a hole 74, through which the electrical cable 52 passes. The cap 72 is filled with a conventional potting material 76, into which an end portion of the electrical cable 52, the copper connectors 58, and end portions of the sleeves 30 and of the electrodes 20 are embedded.

The sensor 10 may be made in a wide range of possible lengths. When the sensor 10 is used, a direct current voltage is applied across the wire conductors 54, which define an open circuit. If the sensor 10 is exposed to an electrically conductive liquid, which passes through the apertures 32 and contacts the electrodes 30, a short circuit is caused. The short circuit is detectible by an ohmmeter r amperage meter (not shown) or by any other means (not shown) used to detect short circuits in liquid detectors known heretofore.

In the preferred embodiment, each electrode 20 is a ribbon having two broad faces and two narrow edges. Alternatively, each electrode 20 may have a different shape, such as round, square, or oblong in cross-section.

Various other modifications may be made in the preferred embodiment described above without departing from the scope and spirit of this invention.

We claim:

1. An elongate, flexible sensor for sensing an electrically conductive liquid, the sensor comprising two flexible electrodes extending along the sensor, each electrode being made from a rubber-like, polymeric material filled with conductive particles, and two flexible sleeves extending along the sensor and being attached to each other along the sensor, each sleeve extending loosely around an associated one of the electrodes and being made from an electrically non-conductive material, the sleeves having multiple apertures enabling such a liquid reaching the sensor to pass through the sleeves so as to cause a short circuit between the electrodes.

2. The elongate sensor of claim 1 wherein the sleeves are braided from a filamentary material so as to define said apertures.

3. The elongate sensor of claim 2 wherein the sleeves are braided from a polyester material.

4. The elongate sensor of claim 3 wherein the sleeves are attached adhesively to each other along the sensor.

5. An elongate, flexible sensor for sensing an electrically conductive liquid the sensor comprising two electrodes extending along the sensor, each electrode being made from a carbon-filled, silicone rubber material, and two flexible sleeves extending along the sensor and being attached to each other along the sensor, each sleeve extending around an associated one of the electrodes and being braided from a filamentary, electrically non-conductive, polymeric material so as to define multiple apertures enabling such a liquid reaching the sensor to pass through the sleeves so as to cause a short circuit between the electrodes.

6. An elongate, flexible sensor for sensing an electrically conductive liquid, the sensor comprising two electrodes extending along the sensor, each electrode being a ribbon made from a carbon-filled, silicone rubber material, and two flexible sleeves extending along the sensor and being attached to each other along the sensor, each sleeve extending around an associated one of the electrodes and being braided from a filamentary, electrically non-conductive, polymeric material so as to define multiple apertures enabling such a liquid reaching the sensor to pass through the sleeves so as to cause a short circuit between the electrodes.

* * * * *